US007524296B2

(12) United States Patent
Patterson et al.

(10) Patent No.: US 7,524,296 B2

(45) **Date of Patent: *Apr. 28, 2009**

(54) SECURE FIT ORTHOPEDIC BRACE HAVING A VACUUM CHAMBER AND ASSOCIATED METHODS

(76) Inventors: William S. Patterson, 1109 Windsong Rd., Orlando, FL (US) 32806; Robert Gailey, 7641 SW. 126th ST., Miami, FL (US) 33156; Augusto Sarmiento, 10333 SW. 72nd Ave., Miami, FL (US) 33156; Maitland C. MacKenzie, 1811 Wind Harbor Rd., Orlando, FL (US) 32809; Roy P. McMurray, 11040 S. Tropical Trail, Merrit Island, FL (US) 32952

( * ) Notice: Subject to any disclaimer, the term of this patent is extended or adjusted under 35 U.S.C. 154(b) by 0 days.

This patent is subject to a terminal disclaimer.

(21) Appl. No.: 11/374,400

(22) Filed: Mar. 13, 2006

(65) Prior Publication Data

US 2006/0155228 A1 Jul. 13, 2006

Related U.S. Application Data

(62) Division of application No. 11/022,226, filed on Dec. 23, 2004, now Pat. No. 7,011,640.

(60) Provisional application No. 60/554,042, filed on Mar. 17, 2004.

(51) Int. Cl.
*A61F 5/00* (2006.01)

(52) U.S. Cl. .............................. 602/13; 602/5; 602/16; 602/23; 602/26; 128/882

(58) Field of Classification Search ..................... 602/5, 602/16, 26, 23, 60–63, 13; 128/846, 869, 128/845, 882; 606/53, 54
See application file for complete search history.

(56) References Cited

U.S. PATENT DOCUMENTS

| | | | | |
|---|---|---|---|---|
| 3,581,741 | A * | 6/1971 | Rosman et al. | 602/16 |
| 3,745,998 | A * | 7/1973 | Rose | 602/6 |
| 4,489,718 | A * | 12/1984 | Martin | 602/16 |
| 4,628,945 | A * | 12/1986 | Johnson, Jr. | 602/27 |
| 4,657,003 | A * | 4/1987 | Wirtz | 128/869 |
| 4,768,501 | A * | 9/1988 | George | 602/6 |
| 4,848,364 | A * | 7/1989 | Bosman | 128/849 |
| 5,025,782 | A * | 6/1991 | Salerno | 602/16 |
| 5,107,823 | A * | 4/1992 | Fratesi | 602/16 |
| 5,399,152 | A * | 3/1995 | Habermeyer et al. | 602/23 |
| 5,458,565 | A * | 10/1995 | Tillinghast et al. | 602/26 |
| 5,718,669 | A * | 2/1998 | Marble | 602/5 |
| 5,807,294 | A * | 9/1998 | Cawley et al. | 602/26 |
| 5,865,772 | A * | 2/1999 | George | 602/3 |
| 6,066,107 | A * | 5/2000 | Habermeyer | 602/6 |
| 6,074,355 | A * | 6/2000 | Bartlett | 602/16 |

(Continued)

*Primary Examiner*—Kim M Lewis

(57) ABSTRACT

The vacuum orthopedic brace and method include the use of an inner sleeve or liner, and at least one rigid member. The rigid member includes a fabric liner or other porous material to act as a wick, and a gasket surrounding the wick material. A valve is preferably provided in the rigid member for drawing air from between the rigid member and the liner, i.e. to create a vacuum. Furthermore, an external, internal or integrated chamber or rigid reservoir is preferably included, and is in communication with the wick filled area between the rigid member and liner, to hold a vacuum.

17 Claims, 2 Drawing Sheets

12/14
24
26
SKIN
28
20
15
13
30
22

U.S. PATENT DOCUMENTS 6,325,773 B1 * 12/2001 Opel .......................... 602/26
6,527,733 B1 * 3/2003 Ceriani et al. ................ 602/16
7,011,640 B2 * 3/2006 Patterson et al. ............. 602/13

* cited by examiner

SECURE FIT ORTHOPEDIC BRACE HAVING A VACUUM CHAMBER AND ASSOCIATED METHODS

CROSS REFERENCE TO RELATED APPLICATIONS

This application is a divisional application claiming priority of U.S. patent application Ser. No. 11/022,226 filed Dec. 23, 2004 now U.S. Pat. No. 7,011,640 and which claims the benefit of U.S. Provisional Application No. 60/554,042 filed on Mar. 17, 2004.

FIELD OF THE INVENTION

The present invention relates to the field of orthopedic braces.

BACKGROUND OF THE INVENTION

When a joint has been injured, orthopedic braces often are used to stabilize and protect the joint during the rehabilitation process. Such orthopedic braces may be used for postoperative support and/or to preventive further injury. A typical brace includes rigid structural components dynamically linked together by hinges, such that the axes of the hinges align with the joint being stabilized. Conventionally, the rigid structural components are secured to the body of the wearer above and below the joint by flexible straps to support and protect the joint when the wearer is active.

For example, when the knee is injured, a knee brace can be used to stabilize the knee joint which connects the upper leg or femur with the lower leg or tibia. Typical knee braces comprise an upper leg cuff that generally conforms to the shape of the upper leg above the knee joint and a lower leg cuff which generally conforms to the shape of the lower leg below the knee joint. The upper and lower leg cuffs are connected to each other by hinges in alignment with the knee joint. A plurality of straps are typically used to secure the cuffs to the leg. Such straps are adjustable and are periodically re-tightened as the brace becomes loose due to fluid loss in the joint and leg from compression associated with the tightened cuffs.

For example, U.S. Pat. No. 6,623,439 to Nelson et al. is directed to a knee brace secured to the leg with a plurality of straps. Also, U.S. Pat. No. 4,628,945 to Johnson, Jr. is directed to an inflatable ankle brace including air-inflatable liners and fastener straps. Additionally, U.S. Pat. No. 5,399,152 to Habermeyer et al. is directed to a fracture brace including evacuatable cushions between the body and outer shell portions which are secured with a clamping element.

It is important to maintain close contact between the limb and the orthopedic brace. Otherwise, the inevitable reduction in the degree of swelling that necessarily follows an injury, and/or the associated fluid loss from compression of the brace, produces a loss of "fit" of the brace. With traditional braces, frequent tightening of the fit of the appliance is strongly urged. However, compliance is frequently ignored, or the value of the advice is not truly understood.

SUMMARY OF THE INVENTION

The present invention includes a vacuum system and orthopedic brace that effectively prevents the loss of firm contact between the limb and the brace, therefore minimizing, if not completely eliminating the traditional adverse changes.

The present invention is directed to a vacuum orthopedic brace and method including the use of an inner sleeve or liner, and at least one rigid member. The rigid member includes a fabric liner or other porous material to act as a wick, and a gasket surrounding the wick material. A valve is preferably provided in the rigid member for drawing air from between the rigid member and the liner, i.e. to create a vacuum. Furthermore, an external, internal or integrated chamber or rigid reservoir is preferably included, and in communication with the wick filled area between the rigid member and liner, to hold a vacuum.

The sleeves are preferably made of polyurethane or silicone, the sleeves may be single-piece sleeves or multi-piece sleeves, and may be tubular and slidable onto the an arm or leg, or the sleeves may be wrap-around type sleeves with a sealing edge, e.g. sealing tape, to ease the installation of the sleeves and brace. A disconnectable hand-pump or otherwise actuated pump may be used to connect to the valve and draw the vacuum between the rigid member and the liner or skin.

FURTHER DESCRIPTION OF THE PREFERRED EMBODIMENTS

The present invention will now be described more fully below with reference to the accompanying drawings, in which preferred embodiments of the invention are shown. This invention may include different embodiments and should not be construed as limited to the embodiments set forth below. These embodiments are provided so that the disclosure will be thorough and complete, and will fully convey the scope of the invention to those skilled in the art. The dimensions of layers and regions may be exaggerated in the figures for greater clarity.

Figure 1:
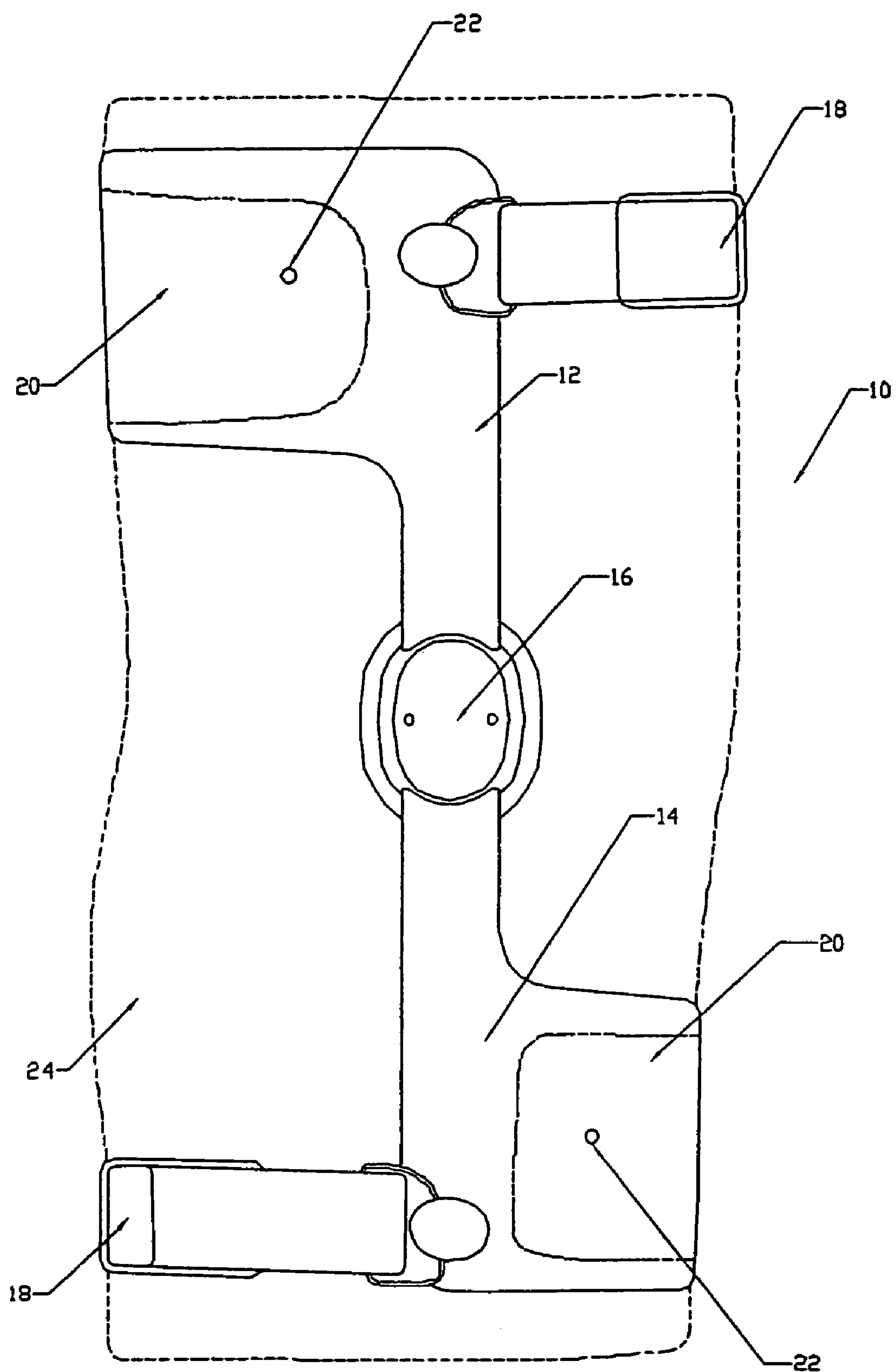
FIG. 1 is a side-view of an example of an orthopedic brace of the present invention.
Figure 2:
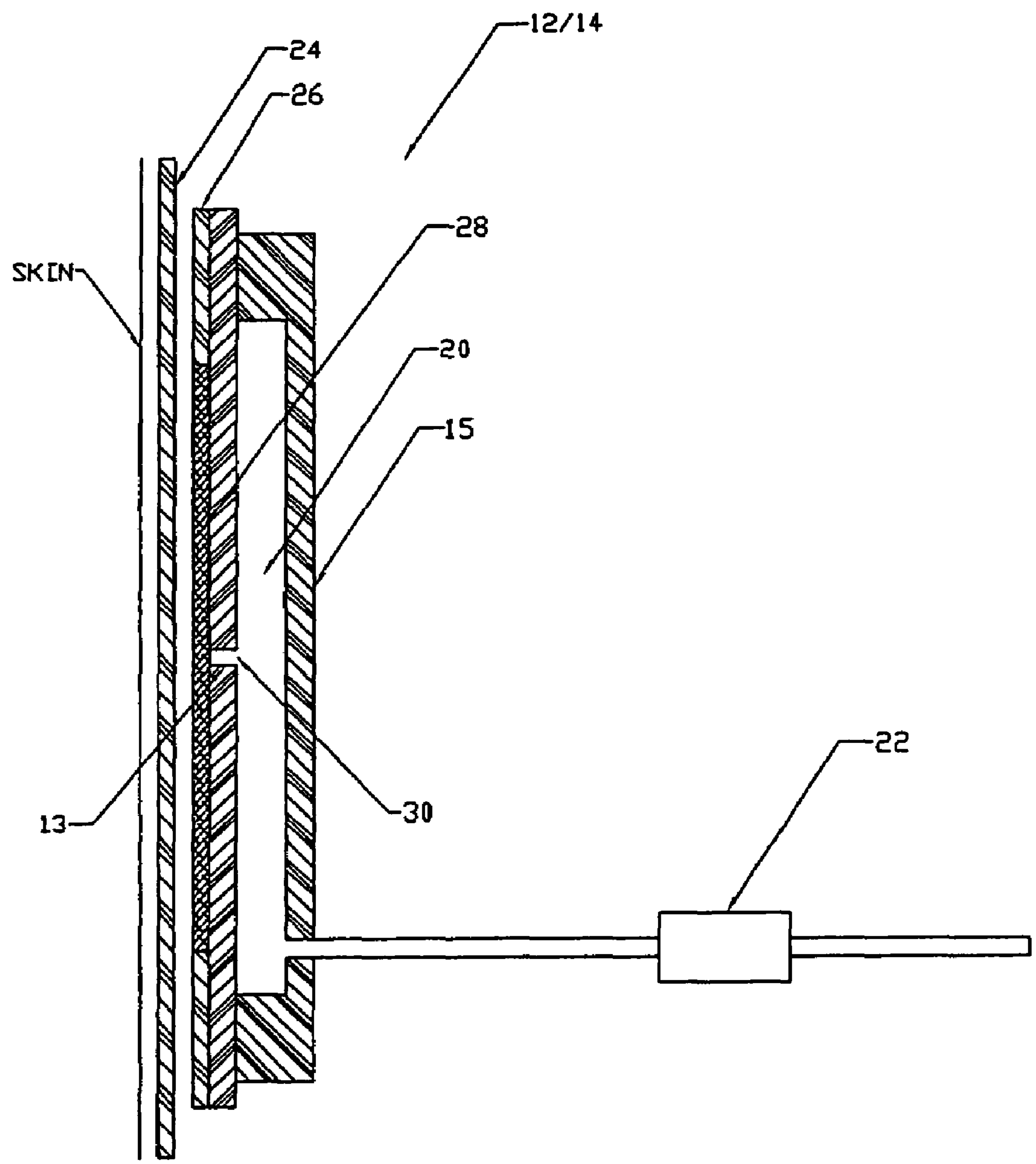
FIG. 2 is a cross-sectional view of a cuff of the brace of FIG. 1.

Referring to FIGS. 1-2, an orthopedic brace 10 is shown, for example, for placement on a leg of a human being. In other words, in this example, the brace 10 is a knee brace, but the invention applies to all types of orthopedic braces including braces for use with feet, ankles, hips, pelvis, back, neck, shoulders, elbows, wrists and hands, for example, as would be appreciated by those skilled in the art.

FIG. 1 illustrates a preferred embodiment of a orthopedic knee brace 10 according to the present invention. The illustrated brace 10 is intended for use on the left leg and includes a first or upper cuff 12 (or rigid member) for positioning above the knee joint and a second or lower cuff 14 (or rigid member) for positioning below the knee joint, and one or more hinges 16 (e.g. polycentric hinges) located along the axis of the knee joint, on one or both sides thereof. Each cuff 12, 14 is preferably a generally U-shape structure, which, for example, may be fabricated of a polymer plastic, carbon fiber material or any other suitable rigid or semi-rigid material appropriate for orthopedic braces.

The brace 10 maintains the associated body portions in proper alignment and thereby prevents injuries caused by lateral joint displacement. The hinges 16 may be configured with a limited range of rotation to prevent hyperextension of the joint. The brace 10 may also be provided with a plurality of straps for securing first cuff 12 and the second cuff 14 to the associated portions of the extremity. The illustrated brace 10 is preferably used to prevent injuries to the joint; however, the brace may also be used to support the joint during rehabilitation after an injury.

While FIG. 2 shows only a cross-sectional view of the upper cuff 12, it is to be understood that the following description thereof regarding the vacuum feature defined below applies also to the lower cuff 14. Each cuff 12, 14 includes an inner wall 13 for placement towards the skin of the user. As mentioned above, a liner 24 is preferably used as a skin interface between the brace and the skin of the user. However, a particular application of the brace may lend itself to the use of the cuffs without the liner 24.

The inner wall 13 of the cuff includes a sealing gasket 26 around a periphery thereof. An outer rigid wall 15 is carried by the inner wall and defines a vacuum reservoir 20 therebetween. A porous or wick material, such as felt or Dacron, for example, is within the area surrounded by the gasket 26. A valve 22 (e.g. one way valve) is in communication with the wick filled area, via hole 30, for drawing air therefrom, i.e. to create a vacuum. Furthermore, the integrated vacuum reservoir or rigid reservoir 20 is preferably included, and in fluid communication with the wick filled area between the cuff and liner 24, to hold a vacuum. Such a reservoir may also be external to the cuff. As discussed, a disconnectable hand-pump or otherwise actuated pump may be used to connect to the valve 22 and draw the vacuum between the cuff and the liner or skin.

In operation, the brace 10 is placed at the treatment site of a user and the cuffs 12, 14 are positioned about the involved limb structure with the liner 24 therebetween. Once properly positioned, a pump is used to draw air from the wick filled area via the valve 22 and communication hole 30. The vacuum chamber is also charged with a vacuum to maintain the vacuum in the wick filled area between the cuff and the liner 24. Support straps 18 may also be used to aid in installation of the brace but do not need to be retightened or adjusted while the brace is being worn. The vacuum feature of this orthopedic brace effectively prevents the loss of firm contact between the limb and the brace, therefore minimizing, if not completely eliminating the typical adverse changes including the loss of fluid in the adjacent limb portions.

The cuffs 12, 14 can be standardized cuffs (i.e. "off the shelf" cuffs) or may be custom molded. The liner 24 may be a tubular sleeve slidable onto the body portion or it may be a wrap-around type sleeve including a sealing overlapping edge. The liner 24 may include separate liner portions associated with each of the cuffs, and the sealing gasket 26 may be formed integrally therewith. The liner 24 is preferably a silicon or urethane liner and may be standardized or custom made as necessary. For example, the liner may be made by body doubling the treatment area of the body portion with pourable silicon, as would be appreciated by the skilled artisan. The ankle area would likely be such a body portion that may benefit from a custom made liner as discussed. Additionally, more than two cuffs may be used if necessary for a specific application.

Advantages of the orthopedic device of the present invention include, but are not limited to: volume control; wound healing; maintaining intimate fit of brace and improving user compliance due to the importance of total contact and an intimate fit with the brace over the treatment site. In the past as the user's body portion would lose contact due to volume loss and the squeezing effect of the brace at the site, the user would have to tighten the brace up by hand which resulted in patient compliance issues and only a certain amount of tightening could be accomplished by the patient or practitioner.

With the orthopedic device of the present invention, i.e. the Vacuum Orthopedic Brace, the tissue rehydration is being accomplished by the vacuum effect being placed on the effected site keeping loss of fluid to that area to a minimum. This in turn may improve healing, e.g. for diabetic patients, and provide another option to surgery.

The above presents a description of the best mode contemplated for a vacuum orthopedic device according to the present invention, and of the manner and process of assembling and using it, in such full, clear, concise, and exact terms as to enable any person skilled in the art to which it pertains to make and use this device. The embodiments described herein are, however, susceptible to modifications and alternate constructions which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the present invention.

The invention claimed is:

1. An orthopedic device for treatment of a body portion comprising:

an inner sleeve to surround the body portion;

at least one rigid member for attachment to the body portion on the inner sleeve, and comprising an inner rigid wall for placement towards the body portion and including at least one hole therein;

an outer rigid wall carried by the inner wall and defining a vacuum reservoir therebetween;

a seal around a periphery of the inner rigid wall adjacent the inner sleeve; and a wick layer carried by the inner rigid wall within the periphery thereof adjacent the inner sleeve to define, with the seal, a vacuum interface area in fluid communication with the vacuum reservoir via the at least one hole; and a valve connected to the vacuum reservoir for evacuating the vacuum reservoir and the vacuum interface area.

2. The orthopedic device according to claim 1 wherein the inner sleeve comprises one of a silicon sleeve and a polyurethane sleeve.

3. The orthopedic device according to claim 1 wherein the seal comprises a urethane gasket.

4. The orthopedic device according to claim 1 wherein the inner sleeve comprises a tubular sleeve slidable onto the body portion.

5. The orthopedic device according to claim 1 wherein the inner sleeve comprises a wrap-around sleeve for wrapping onto the body portion.

6. The orthopedic device according to claim 5 wherein the inner wrap-around sleeve comprises an overlapping sealing edge.

7. The orthopedic device according to claim 1 wherein the at least one rigid member comprises a plurality of rigid members; and the inner sleeve comprises a plurality of sleeve portions respectively associated with the plurality of rigid members.

8. The orthopedic device according to claim 1 further comprising a pump for connection to the valve to evacuate the vacuum reservoir and the vacuum interface area.

9. The orthopedic device according to claim 1 wherein the at least one rigid member further comprises a support device to secure the rigid member to the body portion prior to evacuating the vacuum reservoir and vacuum interface area.

10. An orthopedic device for treatment of a body portion comprising: at least one rigid member for attachment to the body portion and comprising a vacuum interface area, a vacuum reservoir and at least one hole in fluid communication therebetween, and a valve for evacuating the vacuum reservoir and the vacuum interface area; and a seal adjacent the rigid member and defining the vacuum interface area.

11. The orthopedic device according to claim 10 further comprising a wick material within the vacuum interface area.

12. The orthopedic device according to claim 10 wherein the body portion includes a joint; and wherein the at least one rigid member comprises a plurality of rigid members connected by at least one hinge.

13. The orthopedic device according to claim 10 further comprising a pump for connection to the valve to evacuate the vacuum reservoir and the vacuum interface area.

14. A method of treating a body portion with an orthopedic device comprising: attaching at least one rigid member to the body portion, the rigid member comprising a vacuum interface area, a vacuum reservoir and at least one hole in fluid communication therebetween, and a valve for evacuating the vacuum reservoir and the vacuum interface area; providing a seal adjacent the vacuum interface area; and evacuating the vacuum reservoir and the vacuum interface area to secure the rigid member to the body portion.

15. The method according to claim 14 wherein the rigid member further comprises a wick material within the vacuum interface area.

16. The method according to claim 14 wherein evacuating comprises connecting a pump to the valve to evacuate the vacuum reservoir and the vacuum interface area.

17. The method according to claim 14 wherein the rigid member further comprises: an inner rigid wall for placement towards the body portion and including the at least one hole therein; and an outer rigid wall carried by the inner rigid wall and defining the vacuum reservoir therebetween.

* * * * *